US007674792B2

(12) United States Patent
Duffy et al.

(10) Patent No.: US 7,674,792 B2
(45) Date of Patent: Mar. 9, 2010

(54) 5(Z)-5-(6-QUINOXALINYLMETHYLIDENE)-2-[2,6-DICHLOROPHENYL)AMINO]-1,3-THIAZOL-4(5H)-ONE

(75) Inventors: Kevin J. Duffy, Collegeville, PA (US); Duke M. Fitch, Collegeville, PA (US); Beth A. Norton, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 220 days.

(21) Appl. No.: 11/726,741

(22) Filed: Mar. 22, 2007

(65) Prior Publication Data
US 2007/0179144 A1    Aug. 2, 2007

Related U.S. Application Data

(63) Continuation of application No. PCT/US2006/022385, filed on Jun. 8, 2006.

(60) Provisional application No. 60/688,671, filed on Jun. 8, 2005.

(51) Int. Cl.
*A61K 31/498* (2006.01)
*C07D 417/06* (2006.01)

(52) U.S. Cl. ........................ 514/249; 544/353

(58) Field of Classification Search .............. None
See application file for complete search history.

(56) References Cited

U.S. PATENT DOCUMENTS

| | | | |
|---|---|---|---|
| 4,971,996 | A | 11/1990 | Shiraishi et al. |
| 5,057,538 | A | 10/1991 | Shiraishi et al. |
| 5,089,516 | A | 2/1992 | Shiraishi et al. |
| 5,143,928 | A | 9/1992 | Cetenko et al. |
| 5,145,753 | A | 9/1992 | Irino et al. |
| 5,202,341 | A | 4/1993 | Shiraishi et al. |
| 5,290,800 | A | 3/1994 | Cetenko et al. |
| 5,306,822 | A | 4/1994 | Cetenko et al. |
| 5,344,749 | A | 9/1994 | Kiekens et al. |
| 5,374,652 | A | 12/1994 | Buzzetti et al. |
| 5,380,634 | A | 1/1995 | Kiekens et al. |
| 5,494,927 | A | 2/1996 | Cetenko et al. |
| 5,523,314 | A | 6/1996 | Bue-Valleskey et al. |
| 5,554,767 | A | 9/1996 | Wang et al. |
| 5,565,403 | A | 10/1996 | Vanmaele et al. |
| 5,618,835 | A | 4/1997 | Wu et al. |
| 5,661,168 | A | 8/1997 | Panetta et al. |
| 5,716,975 | A | 2/1998 | Bue-Valleskey et al. |
| 5,747,517 | A | 5/1998 | Panetta et al. |
| 5,750,712 | A | 5/1998 | Yoneda et al. |
| 5,843,970 | A | 12/1998 | Pershadsingh et al. |
| 5,958,957 | A | 9/1999 | Andersen et al. |
| 6,011,031 | A | 1/2000 | Lohray et al. |
| 6,221,613 | B1 | 4/2001 | Salon et al. |
| 6,251,928 | B1 | 6/2001 | Panetta et al. |
| 6,372,742 | B1 | 4/2002 | Chin et al. |
| 6,410,734 | B1 | 6/2002 | Hu et al. |
| 6,452,014 | B1 | 9/2002 | Akama et al. |
| 6,518,268 | B1 | 2/2003 | Chin et al. |
| 6,583,140 | B2 | 6/2003 | Hu et al. |
| 6,632,947 | B2 | 10/2003 | Giles et al. |
| 6,685,767 | B2 | 2/2004 | Noro et al. |
| 6,689,491 | B1 | 2/2004 | Nii et al. |
| 6,720,345 | B1 | 4/2004 | Luengo et al. |
| 7,087,758 | B2 | 8/2006 | Bryan et al. |
| 7,160,870 | B2 | 1/2007 | Erickson-Miller et al. |
| 2002/0155381 | A1 | 10/2002 | Berneth et al. |
| 2004/0009527 | A1 | 1/2004 | Dong et al. |
| 2004/0097566 | A1 | 5/2004 | Pfal et al. |
| 2005/0019825 | A9 | 1/2005 | Dong et al. |
| 2005/0042213 | A1 | 2/2005 | Gelder et al. |
| 2006/0004045 | A1 | 1/2006 | Chen et al. |
| 2006/0004046 | A1 | 1/2006 | Chen et al. |
| 2006/0063805 | A1 | 3/2006 | Chen et al. |
| 2006/0106058 | A1 | 5/2006 | Burgess et al. |
| 2006/0293338 | A1 | 12/2006 | Hasegawa et al. |
| 2007/0021447 | A1 | 1/2007 | Church et al. |

FOREIGN PATENT DOCUMENTS

| | | |
|---|---|---|
| DE | 270072 A1 | 7/1989 |
| EP | 554834 A2 | 11/1993 |
| JP | 55045648 | 3/1980 |
| JP | 01097926 | 4/1989 |
| JP | 05002200 A2 | 1/1993 |
| JP | 05333468 | 12/1993 |
| JP | 06128234 | 5/1994 |
| JP | 08109176 | 4/1996 |
| JP | 09255669 A | 9/1997 |
| WO | WO 96/26207 | 8/1996 |
| WO | WO 99/59586 | 11/1999 |
| WO | WO 00/18748 | 4/2000 |
| WO | WO 02/06245 | 1/2002 |
| WO | WO2005/070042 | 8/2005 |
| WO | WO2005/076854 | 8/2005 |
| WO | WO2005/082363 | 9/2005 |
| WO | WO2005/082901 | 9/2005 |

(Continued)

OTHER PUBLICATIONS

Wolff, Manfred E. Burger's Medicinal Chemistry, 5th Ed. Part 1, pp. 975-977 (1995).*

(Continued)

*Primary Examiner*—Emily Bernhardt
(74) *Attorney, Agent, or Firm*—Wayne J. Dustman; Edward R. Gimmi; Charles M. Kinzig

(57) ABSTRACT

Invented is the compound (5Z)-5-(6-quinoxalinylmethylidene)-2-[(2,6-dichlorophenyl)amino]-1,3-thiazol-4(5H)-one, and/or pharmaceutically acceptable salts, hydrates, solvates and pro-drugs thereof. Also invented are pharmaceutical compositions containing this compound, methods of preparing this compound and pharmaceutically acceptable salts, hydrates, solvates and pro-drugs thereof. Also invented are methods of using this compound as an inhibitor of hYAK3 proteins.

7 Claims, 2 Drawing Sheets

FOREIGN PATENT DOCUMENTS

| WO | WO2006/127458 | 11/2006 |
| WO | WO2006/132739 | 12/2006 |
| WO | WO2006/133381 | 12/2006 |

OTHER PUBLICATIONS

Banker et al. "Modern Pharmaceutics", 3rd Ed. p. 596 (1996).*
Vippagunta et al Advanced Drug Delivery Reviews, vol. 48, pp. 3-26 (2001).*
International Search Report and Written Opinion for PCT/US2006/22385 dated Mar. 12, 2007. (5 pages).
Gupta, et al., J. Indian Chem. Soc., 1978, vol. 55, No. 5, pp. 483-485.
Gershuns, et al., Ukrain, Khim. Zhur., 1959, vol. 25, pp. 639-643. (translated).
Burton, et al., J. Med. Chem., 1970, vol. 13, No. 5, pp. 1009-1011.
Foye, et al., J. Pharm. Sci., 1977, vol. 66, pp. 1607-1611.
Akerblom, J. Med. Chem., 1974, vol. 17, pp. 609-615.
Sugasawa, et al., Pharm. Bull., 1953, vol. 1, pp. 281-282.
Walker, J. Chem. Research, Synopses (11), 1913, vol. 460, pp. 1127-1143.
Shikhaliev, Khimicheskaya Tekhnologiya, 2000, vol. 43, No. 2, pp. 95-98. (translated).
Raouf, et al., Acta Chim. Acad. Sci. Hung., 1975, vol. 87, No. 2, pp. 187-193.
Raouf, et al., Acta Chim. Acad. Sci. Hung., 1974, vol. 83, No. 3-4, pp. 359-365.
Harhash, et al., Egypt J. Chem., 1972, vol. 15, No. 1, pp. 11-21.
Pailer, et al., Monatsh. Chem., 1958, vol. 89, pp. 175 and 185. (translated).
Behringer, e tal., Chem. Ber, 1958, vol. 91, 2773 and 2783 or 2773-2783. (translated).
Gilbert, et al., J. Chem. Soc., 1956, pp. 3919-3921.
Brown, et al., J. Chem Soc., 1952, pp. 4397-4400.
Julian, et al., Amer. Chem. Soc., 1935, vol. 57, pp. 1126-1128.
Atti Accad. Naz. Lincei Cl. Sci. Fis. Mat. Nat. Rend., 1906, vol. 15 I, pp. 42. (translated).
Bargellini, Gazz. Chi. Ital., 1906, vol. 36 II, pp. 140-154. (translated).
Andreasch, et al., Monatsh. Chem., 1904, vol. 25, pp. 159-174. (translated).
Andreasch, et al., Monatsh. Chem., 1903, vol. 24, pp. 505-506.
Abdel-Halim, Indian J. of Heterocyclic Chem., 1994, vol. 4, No. 1, pp. 45-50.
Chadha, et al., Indian J. Chem., 1971, vol. 9, No. 9, pp. 910-912.
Bhargava, et al., J. Indian Chem. Soc., 1958, vol. 35, pp. 161-164.
Stieger, Monatsh Chem., 1916, vol. 37, pp. 651. (translated).
Mandlik, et al., J. Univ. Poona, Sci. Technol., 1966, No. 32, pp. 43-46.
Khodair, et al., J. of Heterocyclic Chem., 2002, vol. 39, No. 6, pp. 1153-1160.
Izvestiya Vysshikh Uchebnykh Zavedenii, Khimiya I Khimicheskaya Tekhnologiya, 1979, vol. 22, No. 12, pp. 1445-1448.
Chaudhary, et al., Indian J. of Chem., 1968, vol. 6, No. 9, pp. 488-489.
Mandlik, et al., J. Univ. Poona. Sci. Technol., 1961, vol. No. 1, 20, pp. 41-43.
Shah, et al., J. Indian Chem. Soc., 1959, vol. 36, pp. 731-732.
Das, et al., J. of Scientific & Industrial Research, 1957, vol. 16C, pp. 125-126.
Tyle, et al., Pharmaceutical Research, vol. 3, No. 6, 1986, pp. 318-326.
Lord, et al., Blood, 2000, vol. 95, No. 9. pp. 2838-2846.
Serrano, et al., Nature, 1993, vol. 366, pp. 704-707.
Raap, et al., Eur. J. Org. Chem., 1999, pp. 2609-2621.
Kamb, et al., Science, 1994, vol. 264, pp. 436-440.
Peter & Herskowitz, Cell, 1994, Vol. 79, pp. 181-184.
Plobeck, et al., J. Med. Chem., 2000, vol. 43, pp. 3878-3894.
Kunishima, et al., J. Am. Chem. Soc., 1999, vol. 121, pp. 4722-4723.
Garrett, et al., Mol. Cell. Biol., 1991, vol. 11, pp. 4045-4052.
Johnson, et al., Biochemistry, 2001, vol. 40, pp. 7736-7745.
Arthur Phillips, J. Am. Chem Society, 1945, vol. 67, pp. 744-748.
Stoneham, et al., J. Endocrinology, 1985, vol. 107, pp. 97-106.
Pujari, et al. J. Indian Chem., 1955, vol. 82, No. 7, pp. 431-434.
PCT/US2006/037090 filed Sep. 22, 2006.
PCT/US2006/060511 filed Nov. 3, 2006.
Kim, et al. Biorgan & Med. Chem. Letters 16, 2006, pp. 3772-3776.

* cited by examiner

5(Z)-5-(6-QUINOXALINYLMETHYLIDENE)-2-[2,6-DICHLOROPHENYL)AMINO]-1,3-THIAZOL-4(5H)-ONE

This application is a continuation of International Application No. PCT/US2006/022385 filed Jun. 8, 2006, which claims priority to U.S. provisional Application No. 60/688,671 filed Jun. 8, 2005.

This invention relates to novel compounds useful for inhibiting the hYAK3 protein, specifically (5Z)-5-(6-quinoxalinylmethylidene)-2-[(2,6-dichlorophenyl)amino]-1,3-thiazol-4(5H)-one and pharmaceutically acceptable salts, hydrates, solvates and pro-drugs thereof. This compound is represented by Structure I:

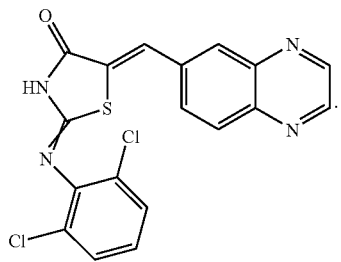

(I)

This invention also relates to the meglumine salt of (5Z)-5-(6-quinoxalinylmethylidene)-2-[(2,6-dichlorophenyl)amino]-1,3-thiazol-4(5H)-one and pharmaceutically acceptable hydrates and solvates thereof. This compound is represented by Structure II:

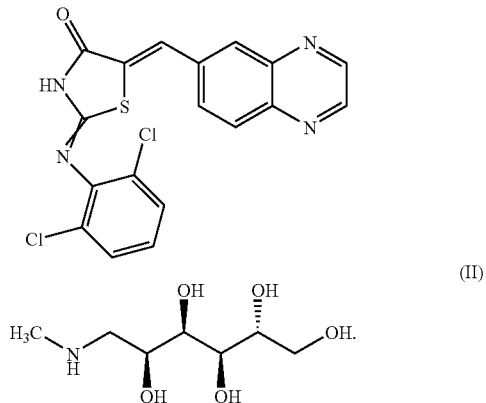

(II)

The compound of this invention, and pharmaceutically acceptable salts, hydrates, solvates and prodrugs thereof, including the meglumine salt, are useful as inhibitors of the hYAK3 protein and for treating or preventing diseases of the erythroid and hematopoietic systems, particularly anemias.

DESCRIPTION OF THE RELATED ART

International Application No. PCT/US2003/037658, having an International filing date of Nov. 18, 2003; which also has International Publication Number WO 2004/047760 and an International Publication date of Jun. 10, 2004, describes a group of thiazolidinone compounds which are indicated as having hYAK3 inhibitory activity and which are indicated as being useful in the treatment of deficiencies in hematopoietic cells, in particular in the treatment of deficiencies in erythroid cells.

International Application No. PCT/US2003/037658 does not specifically disclose (5Z)-5-(6-quinoxalinylmethylidene)-2-[(2,6-dichlorophenyl)amino]-1,3-thiazol-4(5H)-one or its meglumine salt.

DETAILED DESCRIPTION OF THE INVENTION

Figure 1:
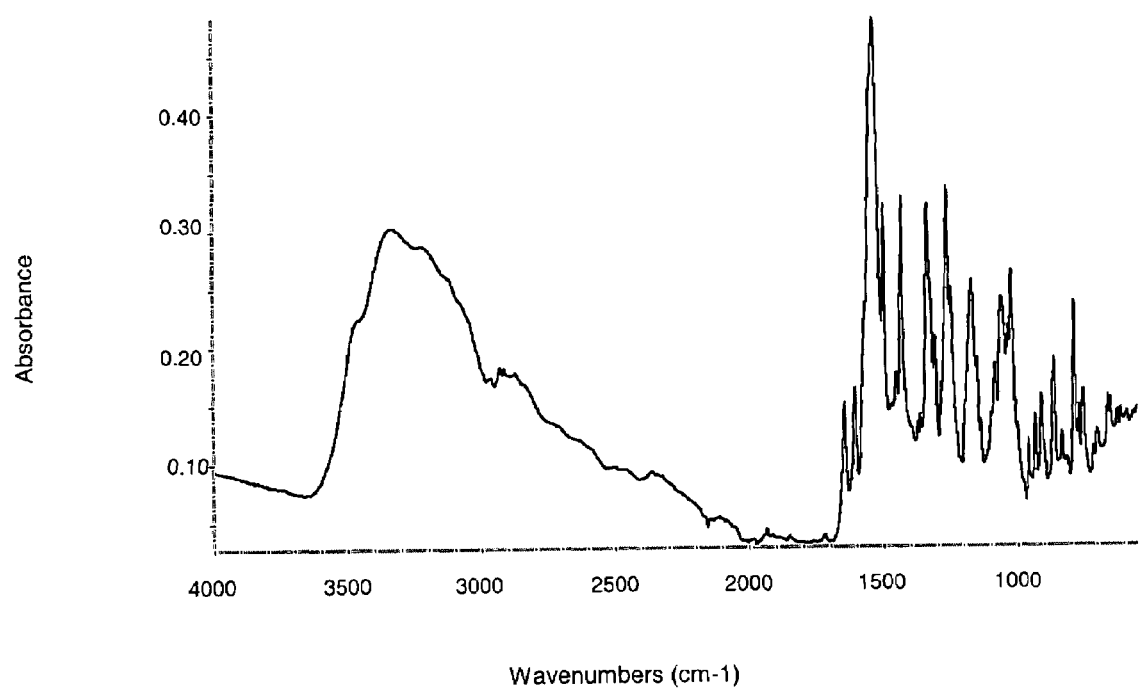
FIG. 1 is an infrared spectra of the (5Z)-5-(6-quinoxalinylmethylidene)-2-[(2,6-dichlorophenyl)amino]-1,3-thiazol-4(5H)-one meglumine hydrate prepared in Example 2.

The present invention is concerned with the novel compound (5Z)-5-(6-quinoxalinylmethylidene)-2-[(2,6-dichlorophenyl)amino]-1,3-thiazol-4(5H)-one and pharmaceutically acceptable salts, hydrates, solvates and pro-drugs thereof (hereinafter—"Compound A"), processes for its preparation, pharmaceutical formulations comprising this compound as an active ingredient, and methods for treating or preventing diseases of the erythroid and hematopoietic systems with Compound A or a pharmaceutical formulation thereof.

The present invention is concerned with the novel compound (5Z)-5-(6-quinoxalinylmethylidene)-2-[(2,6-dichlorophenyl)amino]-1,3-thiazol-4(5H)-one meglumine and pharmaceutically acceptable hydrates and solvates thereof (hereinafter—"Compound D"), processes for its preparation, pharmaceutical formulations comprising this compound as an active ingredient, and methods for treating or preventing diseases of the erythroid and hematopoietic systems with Compound D or a pharmaceutical formulation thereof.

It has been found that Compound A is advantageous over closely related compounds in International Application No. PCT/US2003/037658. The presently invented Compound A has significantly greater aqueous solubility and has significantly increased bioavailability in vivo over the most closely related compounds in International Application No. PCT/US2003/037658.

While the thiazolidinone compounds disclosed in International Application No. PCT/US2003/037658 are useful as inhibitors of the hYAK3 protein, particularly in the treatment of deficiencies in hematopoietic cells in particular in the treatment of deficiencies in erythroid cells, Compound A has the added advantages of enhanced solubility and enhanced bioavailability.

Further, Compound D is useful in that it forms a crystalline compound that is physically and chemically stable. Because Compound D is physically and chemically stable, it is considered non-hygroscopic. Compound D is expected to exhibit solubility similar to Compound A (as the sodium salt) when tested as described in Example 5. Compound D demonstrated bioavailability in the Beagle dog. Suitably, Compound D is in the form of a hydrate. Suitably, Compound D is in the form of a monohydrate. Suitably, Compound D is in the form a monohydrate plus or minus 0.1 equivalent of water. Compound D may also form an anhydrate.

The compounds of this invention, Compound A, including compound D, are useful as inhibitors of the hYAK3 protein, particularly for treating or preventing diseases of the erythroid and hematopoietic systems. Compound A, including compound D, can be administered in a conventional dosage form prepared by combining Compound A, suitably Compound D, with a conventional pharmaceutically acceptable carrier or diluent according to techniques readily known to those of skill in the art, such as those described in International Application No. PCT/US2003/037658. The route of administration may be oral, parenteral or topical. The term parenteral as used herein includes intravenous, intramuscular, subcutaneous, intranasal, intrarectal, intravaginal or intraperitoneal administration. Oral administration is generally preferred.

As used herein, the term "effective amount" means that amount of Compound A, suitably Compound D, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

By the term "treating" and derivatives thereof as used herein, is meant prophylactic and therapeutic therapy.

As used herein, the crisscrossed double bond indicated by the symbol " ⤳ " denotes Z and/or E stereochemistry around the double bond. In other words Compound A, including Compound D, can be either in the Z or E stereochemistry around this double bond, or Compound A, including Compound D, can also be in a mixture of Z and E stereochemistry around the double bond. Further, Compound A, including Compound D, may exist in one tautomeric form or in a mixture of tautomeric forms. An example of one alternative tautomeric form is shown below.

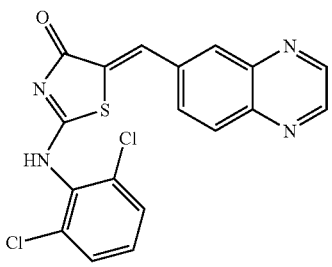

The present invention contemplates all possible tautomeric forms.

By the term "co-administering" and derivatives thereof as used herein is meant either simultaneous administration or any manner of separate sequential administration of Compound A and a further active ingredient or ingredients, known to be useful in treating diseases of the erythroid and hematopoietic systems, particularly anemias, including EPO or a derivative thereof. The term "co-administering" and derivatives thereof as used herein suitably refers to the simultaneous administration or any manner of separate sequential administration of Compound D and a further active ingredient or ingredients, known to be useful in treating diseases of the erythroid and hematopoietic systems, particularly anemias, including EPO or a derivative thereof. The term further active ingredient or ingredients, as used herein, includes any compound or therapeutic agent known to or that demonstrates advantageous properties when administered to a patient in need of treatment for diseases of the erythroid and hematopoietic systems, particularly anemias. Preferably, if the administration is not simultaneous, the compounds are administered in a close time proximity to each other. Furthermore, it does not matter if the compounds are administered in the same dosage form, e.g. one compound may be administered topically and another compound may be administered orally.

Because the novel compounds of the present invention are active as hYAK3 inhibitors they exhibit therapeutic utility in treating diseases of the erythroid and hematopoietic systems, including but not limited to, anemias due to renal insufficiency or to chronic disease, such as autoimmunity, HIV, or cancer, and drug-induced anemias, myelodysplastic syndrome, aplastic anemia, myelosuppression, and cytopenia.

Compound A, including Compound D, are useful in treating diseases of the erythroid and hematopoietic systems, particularly anemias. Such anemias include an anemia selected from the group comprising: aplastic anemia and myelodysplastic syndrome. Such anemias also include those wherein the anemia is a consequence of a primary disease selected from the group consisting of: cancer, leukemia and lymphoma. Such anemias also include those wherein the anemia is a consequence of a primary disease selected from the group consisting of: renal disease, failure or damage. Such anemias include those wherein the anemia is a consequence of chemotherapy or radiation therapy, in particular wherein the chemotherapy is chemotherapy for cancer or AZT treatment for HIV infection. Such anemias include those wherein the anemia is a consequence of a bone marrow transplant or a stem cell transplant. Such anemias also include anemia of newborn infants. Such anemias also include those which are a consequence of viral, fungal, microbial or parasitic infection.

Compound A, including Compound D, are also useful for enhancing normal red blood cell numbers. Such enhancement is desirable for a variety of purposes, especially medical purposes such as preparation of a patient for transfusion and preparation of a patient for surgery.

Compound A, including Compound D, are tested for their ability to inhibit the hYAK3 kinase enzyme by known methods such as those described in International Application No. PCT/US2003/037658.

When tested in in vitro assays for hYAK3 kinase enzyme inhibition, Compound A, as the free acid and as the meglumine salt, exhibited an activity similar to Compound B (described herein) and Compound C (described herein).

The pharmaceutically active compounds of this invention are useful as a hYAK3 inhibitor, suitably in humans, in need thereof.

The present invention therefore provides a method of treating diseases of the erythroid and hematopoietic systems, particularly anemias and other conditions requiring hYAK3 inhibition, which comprises administering an effective amount of Compound A. Compound A also provides for a method of treating the above indicated disease states because of its ability to act as a hYAK3 inhibitor. The drug may be administered to a patient in need thereof by any conventional route of administration, including, but not limited to, intravenous, intramuscular, oral, subcutaneous, intradermal, and parenteral.

The present invention therefore provides a method of treating diseases of the erythroid and hematopoietic systems, particularly anemias and other conditions requiring hYAK3 inhibition, which comprises administering an effective amount of Compound D. Compound D also provides for a method of treating the above indicated disease states because of its ability to act as a hYAK3 inhibitor. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into a convenient dosage form such as a capsule, tablet, or injectable preparation. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, suitably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented Compound A, including Compound D, in a pharmaceutical dosage unit as described above will be an efficacious, nontoxic quantity suitably selected from the range of 0.001-100 mg/kg of total body weight, suitably 0.001-50 mg/kg. When treating a human patient in need of hYAK3 inhibition, the selected dose is administered suitably from 1-6 times daily, orally or parenterally. Preferred forms of parenteral administration include topically, rectally, transdermally, by injection and continuously by infusion. Oral dosage units for human administration suitably contain from 0.05 to 3500 mg of Compound A, or Compound D, suitably from 0.5 to 1,000 mg of Compound A, or Compound D. Oral administration, which uses lower dosages is preferred. Parenteral administration, at high dosages, however, also can be used when safe and convenient for the patient. The above dosages relate to the preferred amount of Compound A and Compound D expressed as the free acid.

It will be recognized by one of skill in the art that the optimal quantity and spacing of individual dosages of Compound A, or Compound D, will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of Compound A, or Compound D, given per day for a defined number of days, can be ascertained by those skilled in the art using conventional course of treatment determination tests.

The method of this invention of inducing hYAK3 inhibitory activity, suitably in humans, comprises administering to a subject in need of such activity an effective hYAK3 inhibiting amount of Compound A.

The method of this invention of inducing hYAK3 inhibitory activity, suitably in humans, comprises administering to a subject in need of such activity an effective hYAK3 inhibiting amount of Compound D.

The invention also provides for the use of Compound A in the manufacture of a medicament for use as a hYAK3 inhibitor.

The invention also provides for the use of Compound D in the manufacture of a medicament for use as a hYAK3 inhibitor.

The invention also provides for the use of Compound A in the manufacture of a medicament for use in therapy.

The invention also provides for the use of Compound D in the manufacture of a medicament for use in therapy.

The invention also provides for the use of Compound A in the manufacture of a medicament for use in treating diseases of the erythroid and hematopoietic systems, particularly anemias.

The invention also provides for the use of Compound D in the manufacture of a medicament for use in treating diseases of the erythroid and hematopoietic systems, particularly anemias.

The invention also provides for a pharmaceutical composition for use as a hYAK3 inhibitor which comprises Compound A and a pharmaceutically acceptable carrier.

The invention also provides for a pharmaceutical composition for use as a hYAK3 inhibitor which comprises Compound D and a pharmaceutically acceptable carrier.

The invention also provides for a pharmaceutical composition for use in the treatment of diseases of the erythroid and hematopoietic systems, particularly anemias, which comprises Compound A and a pharmaceutically acceptable carrier.

The invention also provides for a pharmaceutical composition for use in the treatment of diseases of the erythroid and hematopoietic systems, particularly anemias, which comprises Compound D and a pharmaceutically acceptable carrier.

No unacceptable toxicological effects are expected when a compound of the invention is administered in accordance with the present invention.

In addition, the pharmaceutically active compounds of the present invention can be co-administered with further active ingredients, such as other compounds known to treat diseases of the erythroid and hematopoietic systems, particularly anemias, or compounds known to have utility when used in combination with a hYAK3 inhibitor.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLE 1

Preparation of: (5Z)-5-(6-quinoxalinylmethylidene)-2-[(2,6-dichlorophenyl)amino]-1,3-thiazol-4(5H)-one sodium salt

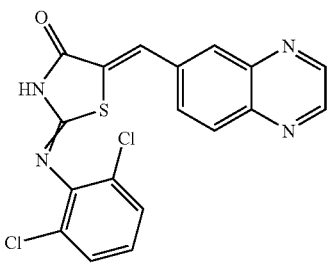

a) 6-Methylquinoxaline. A suspension of 3,4-diaminotoluene (50.0 g; 0.409 mol.) and glyoxal (40% aq. soin.; 52.0 mL; 0.450 mol.) in water (150 mL) and $CH_3CN$ (20.0 mL) was heated to 60° C. for 1 h. Heating was then discontinued and brine (100 mL) was added. The solution was extracted with EtOAc (3×150 mL) and the combined organic layers were dried over $MgSO_4$, filtered, and concentrated in vacuo. Purification via distillation under reduced pressure (120° C., 10 torr) provided 6-methylquinoxaline (48.0 g, 81%) as a clear, colorless oil. 1 H NMR (400 MHz, $CDCl_3$) δ ppm 2.61 (s, 3H) 7.61 (dd, J=8.59, 1.77 Hz, 1H) 7.88 (s, 1H) 8.00 (d, J=8.59 Hz, 1H) 8.79 (dd, J=9.85, 1.77 Hz, 2H) MS(ES+) m/e 145 $[M+H]^+$.

b) Quinoxaline-6-carbaldehyde. A suspension of 6-methylquinoxaline (8.0 g; 0.055 mol.) and selenium dioxide (6.77 g; 0.061 mol.) in 1,4-dioxane (5.0 mL) was irradiated at 200° C. for 30 min. in a Biotage Initiator microwave synthesizer. The above procedure was repeated five further times and the combined, cooled reaction mixtures were dissolved in $CH_2Cl_2$, filtered through a plug of celite, and concentrated in vacuo. Purification via flash column chromatography (silica gel, 20-50% ethyl acetate in hexanes) followed by crystallization from $CH_2Cl_2$ provided quinoxaline-6-carbaldehyde (40.0 g, 91%) as a white solid. $^1$H NMR (400 MHz, $CDCl_3$) δ ppm 10.25 (s, 1H) 8.95 (s, 2H) 8.57 (d, J=1.3 Hz, 1H) 8.24 (dd, J=8.6, 1.5 Hz, 1H) 8.20 (d, J=8.6 Hz, 1H). MS(ES+) m/e 159 $[M+H]^+$.

c) 2-[(2,6-Dichlorophenyl)amino]-1,3-thiazol-4(5H)-one. A suspension of N-(2,6-dichlorophenyl)thiourea (103.7 g; 0.469 mol.) and chloroacetic acid (48.8 g; 0.516 mol.) in glacial acetic acid (600 mL) was stirred and heated under reflux for 2 h. The stirred mixture was allowed to cool to 40° C. then treated dropwise with water (1 L) during which a pale-yellow precipitate formed. The suspension was then filtered and the precipitate washed with water (1 L) to afford the title compound (94.0 g; 79%) as a yellow solid. $^1$H NMR (400 MHz, DMSO-$d_6$) δ ppm 4.10 (s, 2H) 7.14 (t, J=8.08 Hz, 1H) 7.49 (d, J=8.08 Hz, 2H) 12.23 (s, 1H).

d) (5Z)-2-[(2,6-Dichlorophenyl)amino]-5-(6-quinoxalinylmethylidene)-1,3-thiazol-4(5H)-one. A suspension of 2-[(2,6-dichlorophenyl)amino]-1,3-thiazol-4(5H)-one (4.95 g; 0.019 mol.), quinoxaline-6-carbaldehyde (3.00 g; 0.019 mol.) and piperidine (1.88 mL; 0.019 mol.) in ethanol (10.0 mL) was stirred and irradiated at 150° C. for 30 min. in a Biotage Initiator microwave synthesizer. The above procedure was repeated seven further times and the combined, cooled reaction mixtures were poured into water (500 mL) and acidified with 1M aq. HCl (100 mL). The resulting suspension was filtered, washed with water and MeOH, and dried in vacuo to provide (5Z)-2-[(2,6-dichlorophenyl)amino]-5-(6-quinoxalinylmethylidene)-1,3-thiazol-4(5H)-one (47.0 g, 88%) as a dull brown powder. 1 H NMR (400 MHz, DMSO-$d_6$) δ ppm 13.11 (s, 1H) 8.97 (s, 2H) 8.20 (s,1H) 8.17 (d, J=8.6 Hz, 1H) 8.00 (s,1H) 7.96 (dd, J=8.7, 1.6 Hz, 1H) 7.58 (d, J=8.1 Hz, 2H) 7.25 (t, J=8.1 Hz, 1H). MS(ES+) m/e 401 $[M+H]^+$.

e) (5Z)-2-[(2,6-Dichlorophenyl)amino]-5-(6-quinoxalinylmethylidene)-1,3-thiazol-4(5H)-one, sodium salt, 1.75 $H_2O$. A suspension of (5Z)-2-[(2,6-dichlorophenyl)amino]-5-(6-quinoxalinylmethylidene)-1,3-thiazol-4(5H)-one (30.7 g; 0.076 mol.) in water (500 mL) was stirred and treated dropwise with 1M aq. NaOH solution (82.0 mL; 1.08 eq.). The mixture was then stirred and heated under reflux whereupon ethanol was added (100 mL) until complete dissolution occurs. The solution was allowed to cool slowly to room temp. (~4 h) and filtered to give (5Z)-2-[(2,6-dichlorophenyl)amino]-5-(6-quinoxalinylmethylidene)-1,3-thiazol-4(5H)-one, sodium salt, 1.75 hydrate (27.1 g) as yellow needles. Mp. 250-255° C. (broad). Found: % C, 47.19; % H, 2.62; % N, 12.05; % Na, 5.06. $C_{18}H_9Cl_2N_4OSNa$ 1.75 $H_2O$ requires: % C, 47.52; % H, 2.75; % N, 12.32; % Na, 5.07.

EXAMPLE 2

Preparation of: (5Z)-5-(6-quinoxalinylmethylidene)-2-[(2,6-dichlorophenyl)amino]-1,3-thiazol-4(5H)-one meglumine monohydrate A suspension of (5Z)-2-[(2,6-dichlorophenyl)amino]-5-(6-quinoxalinylmethylidene)-1,3-thiazol-4(5H)-one (10.5 mg; 0.0262 mmol.) in acetonitrile (225 uL) was heated to 50° C. and treated with 1M aq. meglumine solution (28.8 uL; 1.1 eq.). The mixture was maintained at 50° C. for approximately two hours then cooled to room temperature and stirred an additional two hours. Filtered and dried in vacuo at 50° C. to give (5Z)-2-[(2,6-dichlorophenyl)amino]-5-(6-quinoxalinylmethylidene)-1,3-thiazol-4(5H)-one, meglumine salt, approximately 1.0 equivalent of water (7.9 mg).

Differential Scanning Calorimetry (DSC) data on Compound D reveals two endothermic events; one at approximately 54° C. and a second event at 158° C.

An infrared spectrum is provided in FIG. 1 appended hereto.

EXAMPLE 3

Preparation of: (5Z)-5-(6-quinoxalinylmethylidene)-2-[(2,6-dichlorophenyl)amino]-1,3-thiazol-4(5H)-one meglumine monohydrate A suspension of (5Z)-2-[(2,6-dichlorophenyl)amino]-5-(6-quinoxalinylmethylidene)-1,3-thiazol-4(5H)-one (5.07 g; 12.64 mmol.) in acetonitrile (101 mL) was heated to 50° C. Seed crystals (seed crystals can be prepared as described in Example 2) were added, and the mixture was slowly treated with 1M aq. meglumine solution (13.3 mL; 1.05 eq.). The mixture was maintained at 50° C. for approximately two hours then cooled to room temp. and stirred an additional two hours. Filtered and dried in vacuo at 50° C. to give (5Z)-2-[(2,6-dichlorophenyl)amino]-5-(6-quinoxalinylmethylidene)-1,3-thiazol-4(5H)-one, meglumine salt, approximately 1.0 equivalent of water (6.78 g).

Found: % C, 48.72; % H, 4.61; % N, 11.30. $C_{18}H_{10}Cl_2N_4OS.C_7H_{17}NO_5.H_2O$ requires: % C, 48.86; % H, 4.76; % N, 11.40.

Differential Scanning Calorimetry (DSC) data on Compound D reveals three endothermic events; one at approximately 54° C., a second event at approximately 101° C., and a third event at approximately 160° C.

Figure 2:
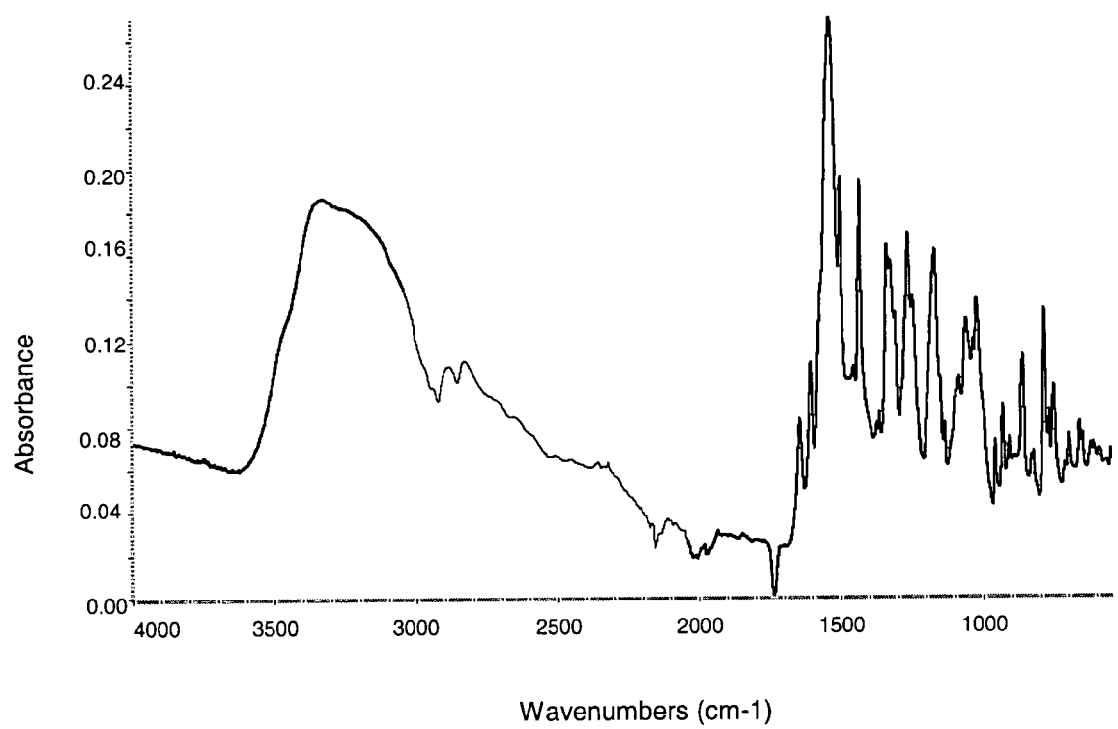
FIG. 2 is an infrared spectra of the (5Z)-5-(6-quinoxalinylmethylidene)-2-[(2,6-dichlorophenyl)amino]-1,3-thiazol-4(5H)-one meglumine hydrate prepared in Example 3.

An infrared spectrum is provided in FIG. 2 appended hereto.

EXAMPLE 4

Alternative Process for the Prepraring the Compounds of the Invention

Process Scheme

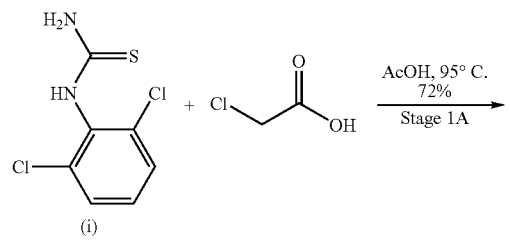

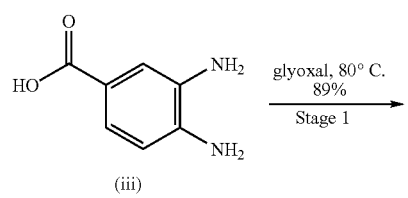

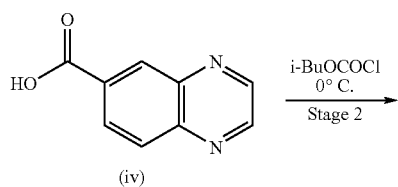

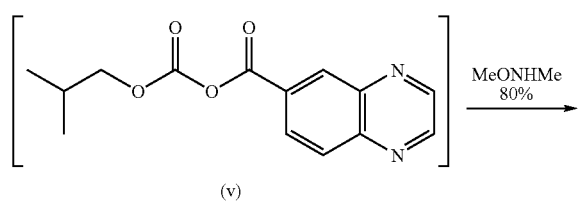

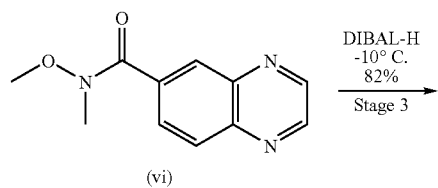

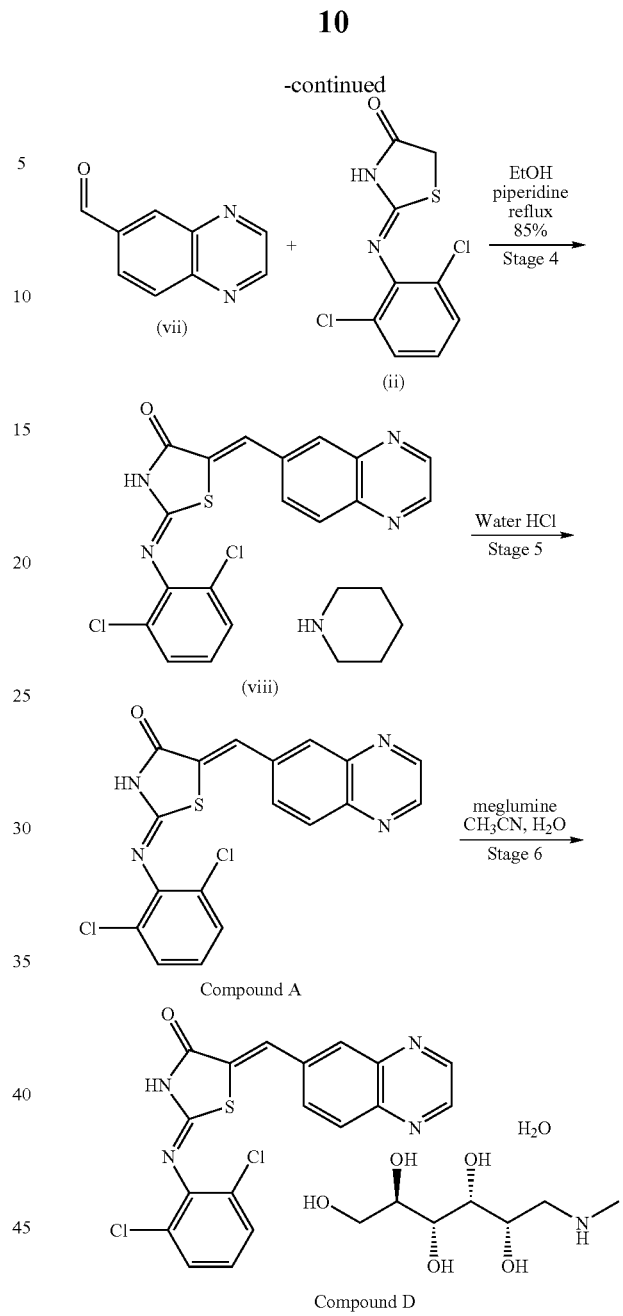

Process Description

Stage 1A

Compound (i) is heated in acetic acid with chloroacetic acid at approximately 95° C. The mixture is cooled to 70° C., diluted with water, and cooled further to 25° C. The product Compound (ii) is filtered off, washed with water, and dried under vacuum at 40° C.

Stage 1

Compound (iii) is heated in ethanol and acetic acid with glyoxal at ~75° C. The resulting suspension is cooled to 5° C. and filtered. The resulting Compound (iv) wetcake is washed with cold ethanol and dried under vacuum at 50° C.

Stage 2

Compound (iv) is stirred as a suspension in THF at 0° C. and treated with isobutylchloroformate followed by N-ethylmorpholine. To the resulting suspension is added N,O-dimethylhydroxyl amine hydrochloride. The suspension is partially concentrated and diluted with ethyl acetate. The resulting organic solution is washed with aqueous sodium bicarbonate and aqueous sodium chloride, partially concentrated, diluted with heptane, and partially concentrated again. The resulting suspension is cooled to 0° C., filtered, washed with cold heptane, and dried under vacuum at 50° C.

Stage 3

A solution of Compound (vi) in THF is treated with a solution of DIBAL-H in toluene at approximately −10° C. The mixture is quenched into aqueous hydrochloric acid and warmed to 20° C. The mixture is diluted with brine. The aqueous phase is removed and backextracted with ethyl acetate. The combined organics are washed with brine, partially concentrated, diluted with heptane, partially distilled again, diluted with heptane, cooled, and filtered. The resulting Compound (vii) wetcake is washed with heptane and dried under vacuum at 50° C.

Stage 4/Stage 5

Compound (ii), Compound (vii), and piperidine are refluxed for ~48 h and the resulting mixture is cooled to 10° C. The resulting solid is filtered solid Compound (viii) is washed with ethanol. The intermediate product is slurried in ethanol and treated with aqueous hydrochloric acid at 20° C. The resulting suspension is filtered, washed with ethanol, water, and ethanol again. Compound A (as the free acid) wetcake is dried under vacuum at 50° C.

Stage 6

Compound A (1.0 eq.) (as the free acid) was suspended at room temperature in 20 vol acetonitrile. The reaction mixture was heated within 45 minutes to Ti=50° C. 0.005 equiv of seeding crystals (seed crystals can be prepared as described in Example 2) were added at 50° C. 1.05 eq of N-methyl-D-glucamine (meglumine) dissolved in 2.6 vol water was added. After the addition, stirring was continued for an additional two hours at 50° C. The reaction mixture was cooled down to 5° C. within 60 minutes and stirring was continued an additional 30 minutes at 5° C. The suspension was filtered and washed two times with 5 vol of 5% water in isopropanol. The solid was then dried under reduced pressure (≦100-50 mbar) at 35° C. and the water content was monitored regularly until it was <4% by KF (Note: ~2.9% is the theoretical hydrate). Compound D resulted.

EXAMPLE 5

An anhydrous form of Compound D is prepared by drying a hydrated form of Compound D in an oven at 50° C. for approximately 6 or more hours.

EXAMPLE 6

Relative Solubilities

The solubility of the sodium salt of Compound A: (5Z)-5-(6-quinoxalinylmethylidene)-2-[(2,6-dichlorophenyl)amino]-1,3-thiazol-4(5H)-one sodium salt, was compared to what is considered to be the two most closely related compounds prepared in International Application No. PCT/US2003/037658. The first is the sodium salt of the compound of example 23 in International Application No. PCT/US2003/037658: 2-(2,6-dichloro-phenylimino)-5-(quinolin-6-ylmethylene)-thiazolidin-4-one sodium salt,

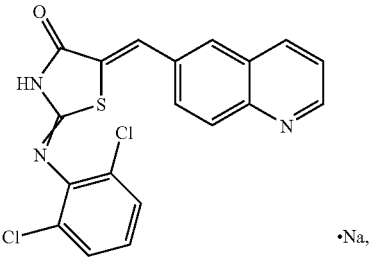

hereinafter (Compound B). The second is the sodium salt of the compound of example 26 in International Application No. PCT/US2003/037658: 2-(2-chloro-phenylimino)-5-(quinoxalin-6-ylmethylene)-thiazolidin-4-one sodium salt,

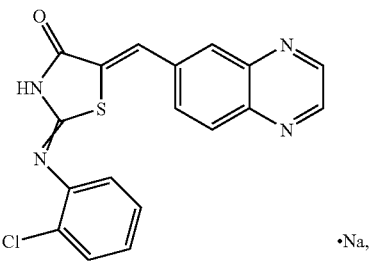

hereinafter (Compound C).

Compounds B and C can be prepared as described in International Application No. PCT/US2003/037658. The sodium salts of these compounds are prepared by methods well known in the art, such as described in Example 1 e) above.

The solubility of each compound was determined as follows: two samples are prepared for each compound. One (the standard sample) contains the compound at a fixed concentration of 20 uM in an aqueous/organic mixed solvent cocktail. The other (the test sample) contains the compound at a maximum total concentration of 200 uM in pH 7.4, 0.05M phosphate buffer. The test sample is spun for 15 minutes to remove any undissovled solid. HPLC analyses are performed on these samples. The relative peak areas are used for computing the solubility. The sodium salt of each compound was used for the comparison. The data are summarized in Table 1 below.

TABLE 1

| Solvent Solubility at 25 deg | Compound A · Na mg/ml | Compound B · Na mg/ml | Compound C · Na mg/ml |
| --- | --- | --- | --- |
| Water pH 7.4 (uM) | 31 | 6 | 0 |

EXAMPLE 7

Bioavailability

The sodium salt of Compound A was fed to male Sprague-Dawley rats by oral gavage in a formulation with 50% PEG- 400, 10% ethanol, 40% of 40% (w/v) aqueous Encapsin in water at a dose of between 1 and 4 mg/kg (16 mL of dose solution per kg). Blood (120 microliters) was sampled at the following time intervals: 0, 20, 40, 60,120,180, 240, 360, 480, and 1440 min. The concentration of Compound A was quantified by LC/MS/Ms analysis of an aliquot (25 microliters blood +25 microliters water) of these samples and the overall blood exposure reported as the Dose-Normalized Area Under the Curve (DNAUC) from a concentration versus time plot and expressed in the units microgram hours per milliliter per minute per kilogram (ug.h/mL/mg/kg). The oral exposures of the sodium salt of Compound B and the sodium salt of Compound C were quantified by the same method.

The data are summarized in Table 2 below.

TABLE 2

| Dose (~1-4 mg/kg) Oral DNAUC rats (Sprague-Dawley) | Compound A · Na mg/ml | Compound B · Na mg/ml | Compound C · Na mg/ml |
|---|---|---|---|
| (ug · h/mL/min/kg) | 1.02 | 0.49 | 0.34 |

The present invention includes within its scope pharmaceutical compositions comprising (5Z)-5-(6-quinoxalinylmethylidene)-2-[(2,6-dichlorophenyl)amino]-1,3-thiazol-4(5H)-one, and/or pharmaceutically acceptable salts, hydrates, solvates and pro-drugs thereof, as the active ingredient, in association with a pharmaceutically acceptable carrier or diluent. The present invention includes within its scope pharmaceutical compositions comprising Compound D and/or pharmaceutically acceptable hydrates and solvates thereof, as the active ingredient, in association with a pharmaceutically acceptable carrier or diluent. The compounds of this invention can be administered by oral or parenteral routes of administration and can be formulated in dosage forms appropriate for each route of administration including capsules, tablets, pills, powders and granules. In such solid dosage forms, the active ingredient is admixed with at least one inert diluent. The oral dosage forms can also comprise, as is normal practice, additional substances other than inert diluents, e.g., lubricating agents, glidants and antioxidants. In the case of capsules, tablets and pills, the dosage forms may also comprise buffering agents. Tablets and pills can additionally be prepared for a sustained release.

Preparations according to this invention for parenteral administration include sterile aqueous solutions although nonaqueous suspensions of emulsions can be employed. Such dosage forms may also contain adjuvants such as preserving, wetting, osmotic, buffering, emulsifying and dispersing agents. They may be sterilized by, for example, filtration through a bacteria retaining filter, by incorporating sterilizing agents into the compositions, irradiating the compositions or by heating the compositions.

The following examples further illustrate the pharmaceutical compositions which are a feature of this invention.

EXAMPLE 8

Tablet Composition

Lactose, microcrystalline cellulose, sodium starch glycolate, magnesium stearate and (5Z)-5-(6-quinoxalinylmethylidene)-2-[(2,6-dichlorophenyl)amino]-1,3-thiazol-4(5H)-one are blended in the proportions shown in Table 3 below. The blend is then compressed into tablets.

TABLE 3

| INGREDIENT | mg. |
|---|---|
| (5Z)-5-(6-quinoxalinylmethylidene)-2-[(2,6-dichlorophenyl)amino]-1,3-thiazol-4(5H)-one | 8 |
| microcrystalline cellulose | 112 |
| lactose | 70 |
| sodium starch glycolate | 8 |
| magnesium stearate | 2 |

EXAMPLE 9

Injectable Parenteral Composition

An injectable form for administering (5Z)-5-(6-quinoxalinylmethylidene)-2-[(2,6-dichlorophenyl)amino]-1,3-thiazol-4(5H)-one meglumine is produced by stirring 5.0 mg. of the compound in 1.0 ml. of normal saline.

EXAMPLE 10

Capsule Composition

An oral dosage form for administering the present invention is produced by filing a standard two piece hard gelatin capsule with the ingredients in the proportions shown in Table 4, below.

TABLE 4

| INGREDIENTS | AMOUNTS |
|---|---|
| (5Z)-5-(6-quinoxalinylmethylidene)-2-[(2,6-dichlorophenyl)amino]-1,3-thiazol-4(5H)-one meglumine | 25 mg |
| Lactose | 55 mg |
| Talc | 16 mg |
| Magnesium Stearate | 4 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. The compound (5Z)-5-(6-quinoxalinylmethylidene)-2-[(2,6-dichlorophenyl)amino]-1,3-thiazol-4(5H-one monosodium salt hydrate thereof.

2. The compound (5Z)-5-(6-quinoxalinylmethylidene)-2-[(2,6-dichlorophenyl)amino]-1,3-thiazol-4(5H-one meglumine salt hydrate thereof in a crystalline form.

3. The compound of claim 1 wherein the compound is the monosodium salt.

4. The compound of claim 1 wherein the compound is a hydrate of the monosodium salt.

5. The compound of claim 4 wherein the hydrate contains less than 5.25 waters of solvation.

6. A pharmaceutical composition comprising the compound of claim 1 and a pharmaceutically acceptable carrier.

7. A pharmaceutical composition comprising the compound of claim 2 and a pharmaceutically acceptable carrier.

* * * * *